United States Patent [19]

Charmillot et al.

[11] Patent Number: 4,765,322

[45] Date of Patent: * Aug. 23, 1988

[54] METHOD OF TREATING NEUROVEGETATIVE DISORDERS AND APPARATUS THEREFOR

[75] Inventors: Rene Charmillot, Delemont; Jean-Pierre Lebet, Montreux, both of Switzerland

[73] Assignee: Symtonic SA, Lausanne, Switzerland

[*] Notice: The portion of the term of this patent subsequent to Mar. 17, 2004 has been disclaimed.

[21] Appl. No.: 27,181

[22] Filed: Mar. 16, 1987

Related U.S. Application Data

[63] Continuation of Ser. No. 612,544, May 21, 1984, Pat. No. 4,649,935.

[51] Int. Cl.⁴ ............................................. A61N 1/32
[52] U.S. Cl. ................................. 128/783; 128/787; 128/421; 128/395
[58] Field of Search ............... 128/1 C, 419 R, 420, 128/421, 422, 423 R, 362, 395-398, 783, 784, 800, 801, 787, 791-795

[56] References Cited

U.S. PATENT DOCUMENTS

| 535,905 | 3/1895 | Horton et al. | 128/787 |
| 1,257,555 | 2/1918 | Vreeland | 128/420 X |
| 1,967,815 | 7/1934 | Freiberg | 128/787 |
| 3,255,753 | 6/1966 | Wing | 128/1 C |
| 3,464,416 | 9/1969 | Williams | 128/1 C |
| 3,762,396 | 10/1973 | Ballantine et al. | 128/1 C |
| 4,305,402 | 12/1981 | Katims | 128/1 C X |
| 4,334,542 | 6/1982 | Takinishi et al. | 128/787 X |

FOREIGN PATENT DOCUMENTS

| 774178 | 12/1967 | Canada | 128/1 C |
| 1554569 | 12/1968 | France | 128/1 C |
| 305439 | 2/1933 | Italy | 128/787 |

Primary Examiner—Lee S. Cohen
Attorney, Agent, or Firm—Browdy and Neimark

[57] ABSTRACT

Disclosed is a method of treating a subject suffering from a neurovegetative disorder, which comprises the step of applying to the brain of said subject, a therapeutically effective amount of an electrically induced energy capable of influencing the vegetative nervous system of the brain, the application of said energy being performed by placing a suitably adapted energy applicator in the mouth or endonasal cavity of the subject and energizing the applicator so that the brain and in particular the limbic system thereof receives electrically induced energy from the applicator.

The electrically induced energy may consist of an electromagnetic wave of field energy, the energy produced by an electric current passing through the brain of said subject, and a combination of such energies.

Apparatus for performing the method and including a generator of the electrically induced energy and the applicator is also disclosed.

11 Claims, 3 Drawing Sheets

METHOD OF TREATING NEUROVEGETATIVE DISORDERS AND APPARATUS THEREFOR

This is a continuation of application Ser. No. 612,544 filed May 21, 1984, now U.S. Pat. No. 4,649,935.

This invention relates to a method of treating a subject suffering from a neurovegetative disorder, and apparatus for performing such treatment. The nature of the neurovegetative disorder which may be treated by the method of the invention may be of various categories, but will generally involve anxiety neurosis.

The common syndrome of anxiety neurosis varies in severity from mild agitation to major incapacitating states of tension. The anxiety itself in acute attacks or wavelike episodes dominates the clinical picture. Obsessions, phobias, hypochondriacal concerns, and other neurotic manifestations may appear. The physiologic manifestations—palpitations, hyperventilation, excessive sweating, tremulousness, insomnia, anorexia—are common complaints. Patients often suffer from fatigue, weakness, and irritability between episodes. Almost any physical disorder that disturbs the homeostasis of an individual may include anxiety as one of its manifestations. Other causes to consider include cardiovascular episodes, hypoglycemia, perforated viscus, internal hemorrhage, or other major disorders of sudden onset. Anxiety neurosis is seen more frequently among patients in a cardiology practice than in other medical practices, emphasizing both the cardiovascular manifestation of anxiety and the anxiety-provoking aspects of heart disease. The management of an anxiety state in a patient recovering from a myocardial infarction may be a critical factor. Such patients may fight sleep and resist tranquilizers because of fear of death.

The method of the invention, for treating a subject suffering from a neurovegetative disorder such as of the nature particularly discussed above, comprises the step of applying to the said subject, a therapeutically effective amount of an electrically induced energy capable of influencing the vegetative nervous system of the brain, the application of said energy being performed by placing a suitably adapted energy applicator in the mouth or endonasal cavity of the subject and energising the applicator so that the brain and in particular the limbic system thereof receives electrically induced energy from the applicator.

Most preferably, in view of convenience and comfort to the patient, the energy applicator is placed in the mouth of the patient such as adjacent or against the palate. Important is that the brain and in particular the limbic system thereof receive energy from the applicator. It has been found in accordance with the invention that the most effective manner, if not the only effective manner, of achieving this is to locate the energy applicator immediately beneath the base of the brain of the subject. The endonasal cavity is a location for the applicator which leads to very satisfactory and excellent therapeutic results in view of close proximity to the base of the brain. However, as mentioned, the applicator is more conveniently located in the mouth of the subject.

The electrically induced energy capable of influencing the vegetative nervous system of the brain may be of a variety of types including particularly an electromagnetic wave energy which is transmitted to the brain with the aid of the energy applicator, which then functions as a transmitter. Other electrically induced energies contemplated include an electromagnetic field energy, the energy produced by an electric current passing through the brain of the subject, and a combination of any two or more of the electrically induced energies mentioned above. Specific electromagnetic wave energies found to be effective in the method of the invention are rectangular d.c. pulses having a pulse duration of from 0.5 to 5 milliseconds at a voltage of from 10 to 100 millivolts with a repetition frequency of from 10 to 100 Hertz and a.c. pulses having a frequency of from 20 to 100 Megahertz modulated with a frequency of modulation of from 2.5 to 6000 Hertz.

Another energy contemplated is electromagnetic waves in the form of a beam of coherent light having a wavelength which corresponds to the visible band of the spectrum of electromagnetic radiation. Where the energy is to include an electric current passing through the brain of the subject, an electrode in contact with the skin of the subject, with a lead back to the power source is required. Since it is particularly required that the brain of the subject receive the electrically induced energy, one or preferably more electrodes are located about the head of the subject, such as particularly behind the ears and/or on the temples of the subject.

As will also become apparent from the description below of apparatus in accordance with the invention, the method of treatment contemplates adjustment of amounts of energy to be applied to the brain of the subject per unit of time. More particularly, some subjects may respond more satisfactorily to electromagnetic waves of high amplitude and others to waves of lower amplitude. Similarly, the frequency of electromagnetic waves may also influence response, so that frequency and also frequency of modulation of a particular electromagnetic wave are also most preferably adjustable.

The method of the invention and apparatus therefor particularly also contemplates a procedure simply involving application of one single type of energy, preferably of electromagnetic nature, at a fixed frequency and fixed amplitude within the ranges mentioned above. Where desired, a frequency of modulation of a.c. pulses may also be fixed within the range mentioned above.

A method involving application of d.c. pulses having a duration within the range mentioned above and a fixed repitition frequency is particularly convenient in that apparatus for applying such electromagnetic wave energy may be battery operated and portable, as in the form of a pocket flashlight. Apparatus of the invention for performing the method of treatment comprises a generator of electrically induced energy capable of influencing the neurovegetative system of the brain, and an energy applicator adapted to be placed in the mouth or endonasal cavity of the subject for applying electrically induced energy received from the generator to the brain of the subject and in particular to the limbic system thereof. More particulars of detailed constructions of apparatus in accordance with the invention can be seen from the description of embodiments with reference to the accompanying drawings. Satisfactory to excellent results have been achieved with the method and apparatus of the invention in the treatment of anxiety neurosis characterised by episodic diffuse anxiety and depressive neurosis characterised by low self-esteem and lowered vitality. Stress and nervousness along with physical symptoms often associated therewith or with anxiety may similarly be treated. Diseases arising from arterial hypertension, coronary diseases, asthma and other symptoms which may be linked with disorders of the vegetative nervous system are exemplary of diseases which may be treated by the method of the invention. Insomnia is a particular symptom which may be successfuly treated as is gastritis or gastro-duodenal disorders which may arise from anxiety, stress or depression.

The following are examples of treatments performed on a variety of subjects suffering from the state of neurosis or disease indicated below. The time over which the electrically induced energy is applied is similary provided. The nature of the electrically induced energy invariably includes electromagnetic radiation, which on its own provides beneficial results:

EXAMPLE 1

Name of patient: G.R.
Date of birth: 1912
Disease: Arteriosclerosis
Symptoms: Anxiety, Insomnia

TREATMENTS AND RESULTS

| Date | Placement of catheter Inf n.c.* | Mid n.c.* | Sup n.c.* | Duration | Results |
|---|---|---|---|---|---|
| 12.6. | | X | | 5' | No result |
| 13.6. | | X | | 5' | No result |
| 14.6. | | X | | 10' | Relaxation |
| 15.6. | | X | | 10' | Relaxation, sleep |
| 16.6. | | X | | 5' | No result |
| 17.6. | | X | | 5' | Relaxation, Sleep |
| 18.6. | | X | | 5' | Relaxation, Sleep |
| 19.6. | | X | | 5' | id. |
| 20.6. | | X | | 5' | Relaxation, Sleep |
| 21.6. | — | — | — | — | Patient wishes to discontinue treatment |

*nasal concha

EXAMPLE 2

Name of patient: G.E.N.
Date of birth: 1940
Disease: Neurotic (Hystery)
Symptoms: Anxiety

TREATMENTS AND RESULTS

| Date | Placement of catheter Inf n.c.* | Mid n.c.* | Sup n.c.* | Duration | Results |
|---|---|---|---|---|---|
| 14.8. | | | X | 5' | No result |
| 15.8. | | | X | 5' | id. |
| 16.8. | | | X | 5' | id. |
| 17.8. | | | X | 5' | id. |
| 18.8. | | | X | 5' | id. |
| 19.8. | | | X | 5' | id. |

*nasal concha

EXAMPLE 3

Name of patient: M.M.
Date of birth: 1940
Disease: Neurotic
Symptoms: Insomnia

TREATMENT AND RESULTS

| Date | Placement of catheter Inf n.c.* | Mid n.c.* | Sup n.c.* | Duration | Results |
|---|---|---|---|---|---|
| 1.8. | | | X | 10' | No result |
| 2.8. | | | X | 5' | Sleep, wishes medication |
| 3.8. | | | X | 5' | id. |
| 5.8. | | | X | 5' | id. |
| 6.8. | — | — | — | — | id. |
| 7.8. | | | X | 5' | id. |
| 8.8. | — | — | — | — | id. |
| 10.8. | | | X | 5' | id. |
| 11.8. | — | — | — | — | Weight gain, Sleep well |
| 12.8. | — | — | — | — | Sleep well |
| 13.8. | | | X | 5' | id. |
| 14.8. | — | — | — | — | Stop treatment due to overweight |

*nasal concha

EXAMPLE 4

Name of patient: J.C.M.
Date of birth: 1945
Disease: Stress
Symptoms: Insomnia

TREATMENTS AND RESULTS

| Date | Placement of catheter Inf n.c.* | Mid n.c.* | Sup n.c.* | Duration | Results |
|---|---|---|---|---|---|
| 27.6. | | | X | 10' | No result |
| 28.6. | | | X | 10' | No result |
| 29.6. | | | X | 10' | Sleep partally |
| 30.6. | | | X | 15' | Sleep without medication |
| 1.7. | | | X | 15' | id. |
| 2.7. | | | X | 15' | id. |
| 3.7. | | | X | 15' | Sleep also during the day |
| 4.7. | — | — | — | — | Insomnia |
| 5.7. | | | X | 10' | Sleep |
| 6.7. | | | X | 10' | Sleep |
| 7.7. | | | X | 10' | Sleep also during the day |
| 8.7. | | | X | 10' | Sleep during the day |
| 9.7. | — | — | — | — | Sleep well |
| 10.7. | — | — | — | — | Insomnia |
| 11.7. | | | X | 5' | Sleep |
| 12.7. | | | X | 5' | Sleep |
| 13.7. | — | — | — | — | Sleep |
| 14.7. | — | — | — | — | Insomnia |
| 15.7. | | | X | 5' | Insomnia |
| 16.7. | | | X | 5' | Sleep |
| 17.7. | — | — | — | — | Insomnia |
| 18.7. | | | X | 5' | Sleep |

*nasal concha

EXAMPLE 5

Name of patient: G.M.
Date of birth: 1948
Disease: Stress
Symptoms: Insomnia

TREATMENTS AND RESULTS

| Date | Placement of catheter Inf n.c.* | Mid n.c.* | Sup n.c.* | Duration | Results |
|---|---|---|---|---|---|
| 13.6. | | | X | 5' | Sleep |
| 14.6. | | | X | 5' | Sleep |
| 15.6. | | | X | 5' | Sleep |
| 16.6. | | | X | 5' | Sleep |
| 17.6. | — | — | — | — | Insomnia |
| 18.6. | | | X | 5' | Sleep |
| 19.6. | — | — | — | — | Insomnia |
| 20.6. | — | — | — | — | Insomnia |
| 21.6. | | | X | 5' | Sleep |
| 22.6. | | X | | 5' | Insomnia |
| 23.6. | | | X | 5' | Sleep |

-continued

Name of patient: G.M.
Date of birth: 1948
Disease: Stress
Symptoms: Insomnia

TREATMENTS AND RESULTS

| Date | Placement of catheter Inf n.c.* | Mid n.c.* | Sup n.c.* | Duration | Results |
|---|---|---|---|---|---|
| 24.6. | | | X | 5' | id. |
| 25.6. | | | X | 5' | id. |
| 26.6. | — | — | — | — | Insomnia |
| 27.6. | — | — | — | — | Insomnia |
| 28.6. | | | X | 5' | Sleep |
| 29.6. | | | X | 5' | id. |

*nasal concha

EXAMPLE 6

Name of patient: C.P.
Date of birth: 1946
Disease: Stress
Symptoms: Anxiety

TREATMENTS AND RESULTS

| Date | Placement of catheter Inf n.c.* | Mid n.c.* | Sup n.c.* | Duration | Results |
|---|---|---|---|---|---|
| 12.6. | | | X | 10' | Relaxation |
| 13.6. | | | X | 10' | Relaxation |
| 14.6. | | | X | 10' | Sleeping during the day |
| 15.6. | — | — | — | — | id. |
| 16.6. | — | — | — | — | Relaxation |
| 17.6. | — | — | — | — | id. |
| 18.6. | | | X | 5' | id. |
| 20.6. | | | X | 5' | id. |
| 22.6. | | | X | 5' | id. |
| 26.6. | | | X | 5' | id. |
| 30.6. | | | X | 5' | id. |
| 2.7. | | | X | 5' | id. |
| | NO TREATMENT | | | | id. |
| | — | — | — | — | id. |
| | — | — | — | — | id. |
| 18.7. | — | — | — | — | id. |

*nasal concha

EXAMPLE 7

Name of patient: C.H.
Date of birth: 1956
Disease: Stress
Symptoms: Insomnia Anxiety

TREATMENTS AND RESULTS

| Date | Placement of catheter Inf n.c.* | Mid n.c.* | Sup n.c.* | Duration | Results |
|---|---|---|---|---|---|
| 26.7. | | | X | 10' | No side effect |
| 27.7. | | | X | 10' | Sleep without medication |
| 28.7. | — | — | — | — | id. |
| 1.8. | | | X | 10' | id. |
| 6.8. | | | X | 10' | id. |
| 11.8. | | | X | 10' | id. |
| 16.8. | | | X | 10' | id. |

*nasal concha

EXAMPLE 8

Name of patient: F.H.
Date of birth: 1936
Disease: Stress
Symptoms: Insomnia

TREATMENTS AND RESULTS

| Date | Placement of catheter Inf n.c.* | Mid n.c.* | Sup n.c.* | Duration | Results |
|---|---|---|---|---|---|
| 26.7. | | | X | 10' | No side effect |
| 27.7. | | | X | 10' | Sleep without medication |
| 28.7. | — | — | — | — | id. |
| 29.7. | — | — | — | — | id. |
| 30.7. | — | — | — | — | id. |
| 1.8. | | | X | 10' | id. |
| 6.8. | | | X | 10' | id. |
| 11.8 | | | X | 10' | id. |
| 16.8. | | | X | 10' | id. |

*nasal concha

EXAMPLE 9

Name of patient: G.B.P.
Date of birth: 1954
Disease: Depression of neurotic origin
Symptoms: Depression

TREATMENTS AND RESULTS

| Date | Placement of catheter Inf n.c.* | Mid n.c.* | Sup n.c.* | Duration | Results |
|---|---|---|---|---|---|
| 13.6. | | | X | 10' | No result |
| 14.6. | | | X | 10' | No result |
| 15.6. | | X | X | 10' | Less anxiety |
| 16.6. | | | X | 10' | id. |
| 17.6. | X | X | X | 15' | id. |
| 18.6. | X | X | X | 15' | General tiredness |
| 19.6. | | | X | 5' | Feel better |
| 20.6. | | | X | 5' | id. |
| 21.6. | | | X | 5' | id. |
| 22.6. | | | X | 5' | General tiredness |
| 23.6. | — | — | — | — | Feel better |
| 24.6. | — | — | — | — | id. |
| 25.6. | | | X | 5' | id. |
| 26.6. | — | — | — | — | id. |
| 27.6. | — | — | — | — | id. |
| 28.6. | — | — | — | — | id. |
| 29.6. | | | X | 5' | id. |
| 3.7. | | | X | 5' | Relaxation |
| 8.7. | | | X | 5' | id. |
| 13.7. | | | X | 5' | id. |
| 17.7. | | | X | 5' | id. |

*nasal concha

EXAMPLE 10

Name of patient: D.R.C.
Date of birth: 1948
Disease: Asthemia of neurotic vegetative origin
Symptoms: id.

TREATMENTS AND RESULTS

| Date | Placement of catheter Inf n.c.* | Mid n.c.* | Sup n.c.* | Duration | Results |
|---|---|---|---|---|---|
| 13.6. | | | X | 10' | No side effect |
| 14.6. | | X | | 10' | No effect, tiredness |
| 15.6. | X | | | 10' | No effect, id. |
| 16.6. | X | X | X | 15' | No effect, id. |
| 17.6. | | X | | 5' | No effect, id. |
| 18.6. | X | | | 5' | No effect, id. |
| 19.6. | X | X | X | 15' | No effect, id. |
| 20.6. | — | — | — | — | Improvement |
| 21.6. | — | — | — | — | id. |

-continued

| | Name of patient: | D.R.C. | | | |
|---|---|---|---|---|---|
| | Date of birth: | 1948 | | | |
| | Disease: | Asthemia of neurotic vegetative origin | | | |
| | Symptoms: | id. | | | |

TREATMENTS AND RESULTS

| | Placement of catheter | | | | |
|---|---|---|---|---|---|
| Date | Inf n.c.* | Mid n.c.* | Sup n.c.* | Duration | Results |
| 22.6. | X | X | X | 15' | Improvement |
| 23.6. | — | — | — | — | id. |
| 24.6. | — | — | — | — | id. |
| 25.6. | — | — | — | — | id. |
| 26.6. | — | — | — | — | id. |
| 27.6. | X | X | X | 15' | Improvement |
| 28.6. | — | — | — | — | id. |
| 24.6. | — | — | — | — | id. |
| 390.6. | — | — | — | — | Feel well |

*nasal concha

EXAMPLE 11

| | Name of patient: | M.D. | | |
|---|---|---|---|---|
| | Date of birth: | 1941 | | |
| | Disease: | Stress | | |
| | Symptoms: | Anxiety | | |

TREATMENTS AND RESULTS

| | Placement of catheter | | | | |
|---|---|---|---|---|---|
| Date | Inf n.c.* | Mid n.c.* | Sup n.c.* | Duration | Results |
| 20.6. | | | X | 10' | No side effect |
| 21.6. | | | X | — | Reaction to the positioning of the catheter |
| 18.7. | | | | | Stop the experimental id. |

*nasal concha

EXAMPLE 12

| | Name of patient: | S.R.V. |
|---|---|---|
| | Date of birth: | 1910 |
| | Disease: | Arteriosclerosis |
| | Symptoms: | Insomnia |

TREATMENTS AND RESULTS

| | Placement of catheter | | | | |
|---|---|---|---|---|---|
| Date | Inf n.c.* | Mid n.c.* | Sup n.c.* | Duration | Results |
| 18.6. | | | X | 5' | No side effect |
| 19.6. | | | X | 5' | Sleep without medication |
| 20.6. | | | X | 5' | id. |
| 21.6. | | | X | 5' | Sleep during the day |
| 22.6. | — | — | — | — | Sleep without medication |
| 23.6. | — | — | — | — | id. |
| 24.6. | — | — | — | — | id. |
| 25.6. | | | X | 5' | id. |
| 26.6. | | | X | 5' | Sleep during the day |
| 27.6. | — | — | — | — | id. |
| 28.6. | — | — | — | — | Normal sleep |
| 29.6. | — | — | — | — | id. |
| 2.7. | | | X | 5' | id. |
| 7.7. | | | X | 5' | id. |
| 12.7. | | | X | 5' | id. |
| 17.7. | | | X | 5' | id. |
| 22.7. | | | X | 5' | id. |

*nasal concha

EXAMPLE 13

| | Name of patient: | V. | | |
|---|---|---|---|---|
| | Date of birth: | 1930 | | |
| | Disease: | Allergic reactions | | |
| | Symptoms: | Asthma | | |

TREATMENTS AND RESULTS

| | Placement of catheter | | | | |
|---|---|---|---|---|---|
| Date | Inf n.c.* | Mid n.c.* | Sup n.c.* | Duration | Results |
| 14.7. | | | X | 10' | No effect |
| 15.7. | | X | | 10' | No effect |
| 16.7. | X | | | 10' | No effect |
| 17.7. | X | X | X | 15' | No effect STOP |

*nasal concha

EXAMPLE 14

| | Name of patient: | N.J. |
|---|---|---|
| | Date of birth: | 1925 |
| | Disease: | Essential Hypertension (Severe) |
| | Symptoms: | Nervousness, Anxiety |

TREATMENTS AND RESULTS

| | Placement of catheter | | | | |
|---|---|---|---|---|---|
| Date | Inf n.c.* | Mid n.c.* | Sup n.c.* | Duration | Results |
| 18.8. | | | X | 10' | No side effect, little relaxation |
| 19.8. | | | X | 10' | Relaxation, stop medication |
| 20.8. | | | X | 10' | Relaxation, stop medication |
| 21.8. | — | — | — | — | Control of Hypertension |
| 22.8. | — | — | — | — | id. |
| 23.8. | | | X | 5' | No medication, Blood Pressure under control! |

*nasal concha

EXAMPLE 15

| | Name of patient: | C.F.R: |
|---|---|---|
| | Date of birth: | 1941 |
| | Disease: | Stress |
| | Symptoms: | Insomnia |

TREATMENTS AND RESULTS

| | Placement of catheter | | | | |
|---|---|---|---|---|---|
| Date | Inf n.c.* | Mid n.c.* | Sup n.c.* | Duration | Results |
| 18.7. | | | X | 10' | Sleep without medication |
| 19.7. | | | X | 10' | id. |
| 20.7. | | | X | 10' | Relaxation (++) during the day |
| 21.7. | | | X | 10' | id. |
| 22.7. | — | — | — | — | Sleep without medication |
| 23.7. | — | — | — | — | id. |
| 24.7. | | | X | 5' | id. |
| 25.7. | | | X | 5' | id. |
| 26.7. | — | — | — | — | id. |
| 27.7. | — | — | — | — | id. |
| 28.7. | — | — | — | — | id. |
| 29.7. | — | — | — | — | id. |
| 30.7. | | | X | 5' | id. |
| 5.8. | | | X | 5' | id. |
| 10.8. | | | X | 15' | id. |
| 17.8. | | | X | 15' | id. |
| 20.8. | — | — | — | — | id. NO MORE SLEEPING PILL |

*nasal concha

EXAMPLE 16

| | Name of patient: | M.J. | | |
|---|---|---|---|---|
| | Date of birth: | 1943 | | |
| | Disease: | Stress | | |
| | Symptoms: | Anxiety, Insomnia | | |
| TREATMENTS AND RESULTS ||||||

| | Placement of catheter | | | | |
|---|---|---|---|---|---|
| Date | Inf n.c.* | Mid n.c.* | Sup n.c.* | Dura-tion | Results |
| 13.8. | | | X | 10' | No side effect. Relaxation |
| 14.8. | | | X | 10' | Relaxation, Stop medication |
| 15.8. | | | X | 10' | id. |
| 16.8. | — | — | — | — | id. |
| 17.8. | | | X | 10' | General tiredness |
| 18.8. | — | — | — | — | Relaxation |
| 19.8. | — | — | — | — | id. |
| 20.8. | — | — | — | — | id. |
| 21.8. | | | X | 5' | id. |

*nasal concha

Exemplary apparatus illustrative of apparatus of the invention and suitable for carrying out the method of the invention will now be described with reference to the accompanying drawings, in which.

Figure 1:
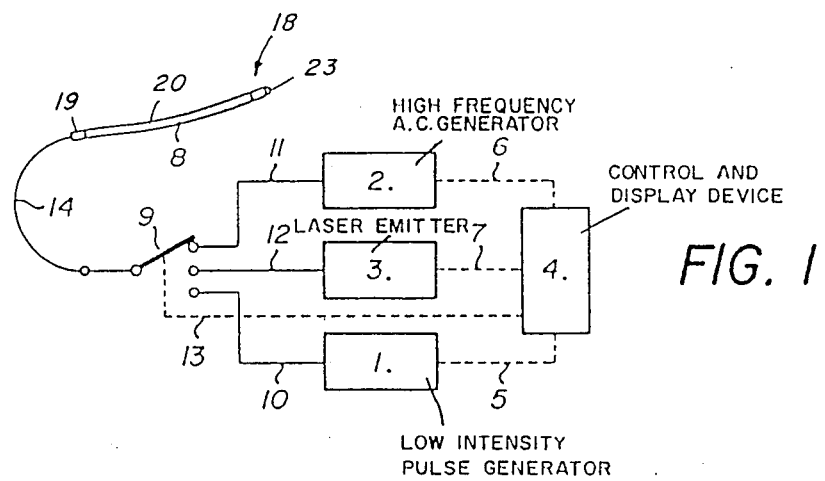
FIG. 1 is a schematic circuit diagram of an apparatus including an applicator.
Figure 2:
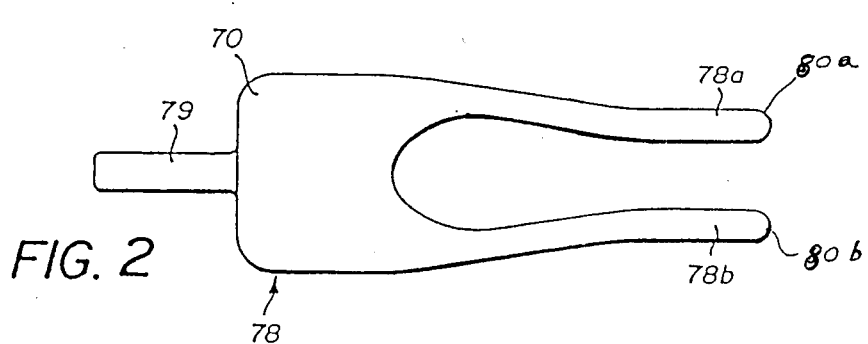
FIG. 2 shows a specific form of an endonasal probe applicator, adapted to be inserted into each nostril of a subject.
Figure 3:
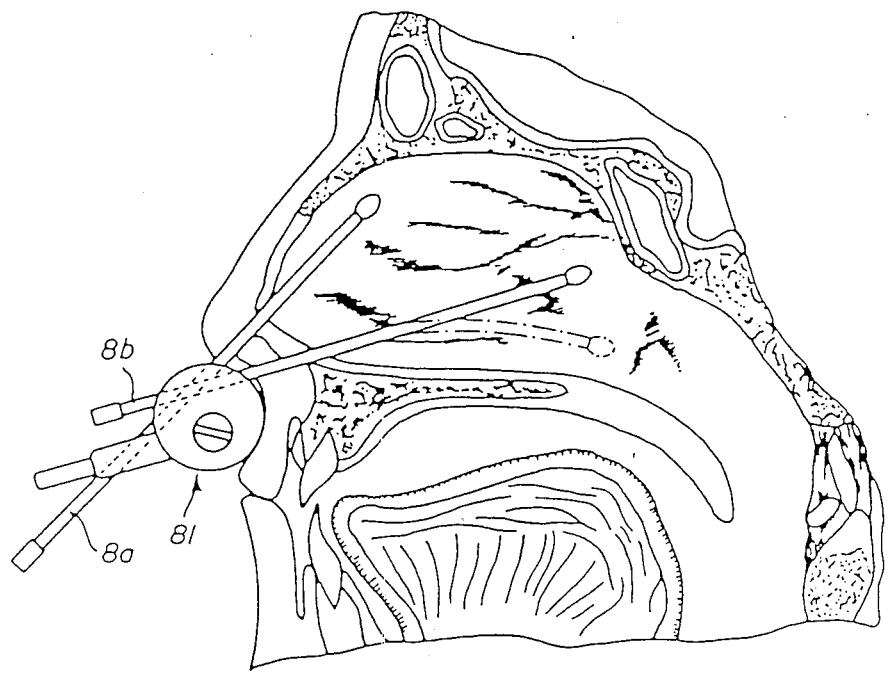
FIG. 3 shows various positions in the endonasal cavity where an applicator, as in FIG. 1 may be located so that the brain of the subject receives electrically induced energy from the applicator.
Figure 4:
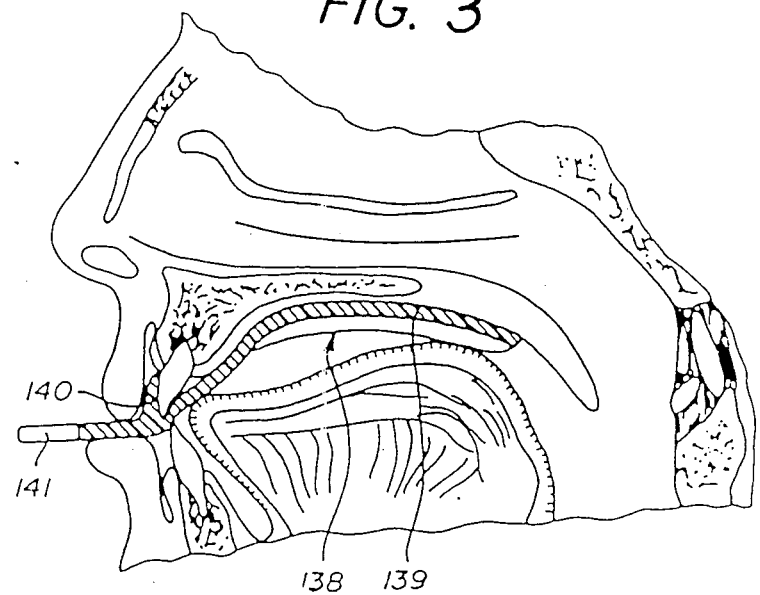
FIG. 4 shows a positioning of an applicator in the mouth of a subject.
Figure 5:
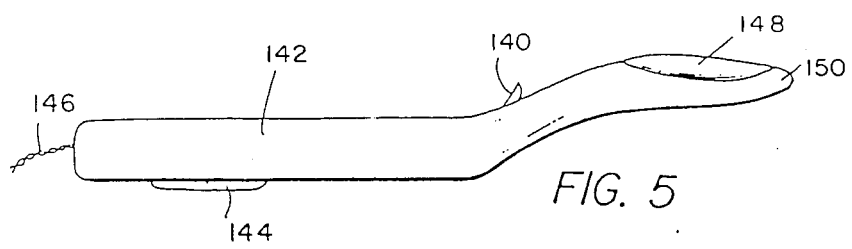
FIG. 5 shows a side elevation of a specific form of an applicator for positioning in the mouth of a subject, as in FIG. 4.
Figure 6:
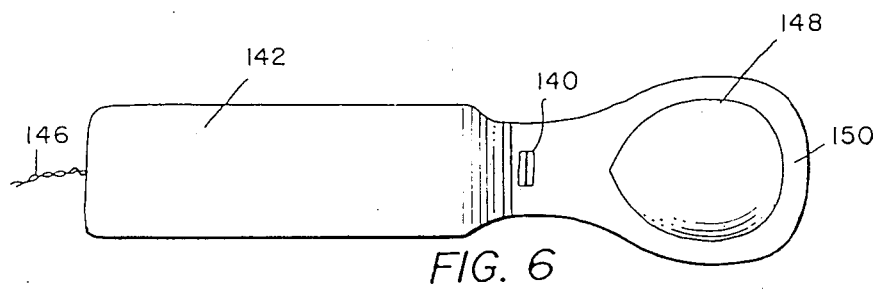
FIG. 6 shows a plan view of the applicator of FIG. 5.
Figure 7A:
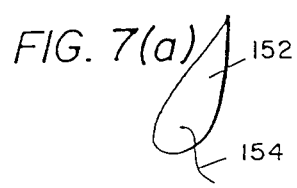
FIGS. 7a, 7b and 7c show alternative forms of electrodes for respectively placing behind the ear of a subject, on a temple of the subject, and about the head of the subject.
Figure 7B:
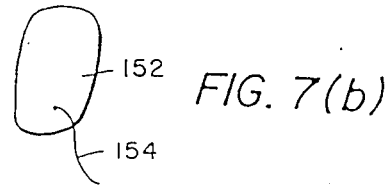
Figure 7C:
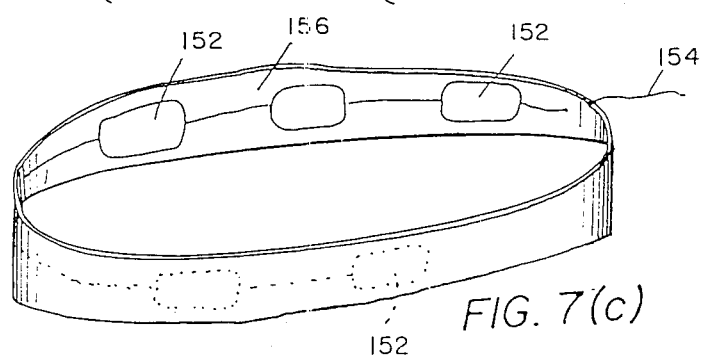

Referring now to FIG. 1 of the drawings, this comprises, by way of example, a device including a plurality of types of electrically induced energy. Thus, the apparatus represented in FIG. 1 comprises a low-frequency d.c. pulse generator 1 capable of producing current pulses in the form of a rectangular signal having, for example, a pulse width of the order of 0.5 to 5 milliseconds with a frequency of 10 to 100 Hertz at a voltage of the order of some tens of millivolts, preferably from 10 to 100 millivolts, a high-frequency a.c. generator 2, modulated at low-frequency, capable of producing an electrical signal formed of sinusoidal wave or square pulses having a frequency of the order of some tens of Megahertz, preferably from 20 to 100 Megahertz, modulated in sinusoidal form with a frequency of modulation of the order of some tens of Hertz, preferably from 2.5 to 6000 Hertz, the power of this generator 2 being preferably of the order of 0.1 to 1 Watt and a generator 3 which is a laser emitter comprising, for example, a Helium-Neon tube capable of emitting a coherent and monochromatic red light beam having a wavelength of 632.8 nanometers in the form of a light signal modulated with a frequency variable from 1 to 160 Hertz. In replacement of the Helium-Neon tube one might equally employ any other suitable source of coherent monochomatic light, for example, a Gallium Arsenide photodiode. A control and display device 4 is connected to the generators 1 and 2, and to laser emitter 3 by respective control signal transmission lines 5, 6 and 7. The control and display device 4 enables the emission of energy by the generators and the laser emitter to be controlled in accordance with the needs of the treatment which it is desired to carry out be means of the apparatus in accordance with a pre-established program in which the characteristics of the luminous electrical signals are made to vary as well as the duration of emission and the sequence of application of each of the signals, and the data of the program so chosen to be displayed. The generators 1 and 2 and the laser emitter 3 are respectively connected to a probe 8 for application of energy, by way of the lines 10 and 11 for transmission of electrical signals and of an optical fibre line 12 for transmission of luminous signals and a switch 9 (shown schematically in FIG. 1) which is likewise controlled by the control and display device 4 by way of a control signal transmission line 13. The switch 9 is arranged so as to enable the signal transmission lines 10, 11 and 12 to be connected individually or simultaneously to the applicator 8 for application of energy, the connection between the applicator 8 and the switch 9 being effected by means of a line 14 for mixed transmission of electrical and luminous signals where desired. The return of the electric current is effected by means of an electrically conductive electrode (see FIGS. 7a, 7b, 7c) during the application of the electrical signals and is connected to the generators 1 and 2 by an electrically conductive line. The applicator 8 shown in FIG. 1 comprises a middle portion 20 consisting of an electrically insulating sheath which is flexible or semi-rigid and, for example, of plastics matter, surrounding an optical fibre line for the transmission of luminous signals, round which may be wound an electrically conductive line for transmission of electrical signals, a front portion 18 intended for placing inside the mouth of endonasal cavity of a patient and a rear portion 19 for connection with the mixed transmission line 14. The front portion 18 of the probe 8 is of a material which is a good electrical conductor, for example of copper or brass. A rounded tip 23 of matter which is transparent or translucent at least for the radiation transmitted to surround an end portion of the optical fibre line for transmission of luminous signals. The rear portion 19 of the applicator 8 comprises a material which is a good electrical conductor, which is for example copper or brass. It will be understood that the front portion 18 of the applicator 8 enables the electrically induced energy to be applied individually or simultaneously, such as in the form of an electromagnetic wave energy or an electric current to the same region of the brain of the subject being treated. The energy applicator 78 shown in FIG. 2 has the general shape of a fork composed of a middle portion 70, two curved arms 78a and 78b and a cylindrical connector rod 79 enabling electrical connection of the applicator to the generators of pulses of electric current and/or of electro-magnetic waves. The applicator 78 may consist of one single piece moulded from plastics material entirely or partially covered with an electrically conductive layer (not shown). Numerous variations may be applied to the form of the applicator 78, especially as for as the spacing, slope and radii of curvature of the arms 78a and 78b are concerned. The dimensions of the applicator may likewise vary, especially in order to allow adaption to the dimensions of the users' nasal cavities as well as to the different exact points of application of the energy. On the other hand the applicator 78 might be equipped with one or more lines for transmission of energy in the form of luminous waves, to play the same part as the optical fibre line in the applicator 8 discussed above. For example, such a line for transmission of energy in the form of luminous waves might consist of a bundle of optical fibres which is incorporated in the body of the applicator 78 which connects the connector rod 79 to the ends of the arms 78a and 78b by dividing in the middle portion 70 into two bundles which continue respectively inside the arms 78a and 78b out to the free ends 80a and 80b of the latter, so as to lie flush with the rounded surfaces of these ends. The support 81 shown in FIG. 3 is illustrative of a means for controlling the depth of penetration and the angle of penetration of a pair of applicators 8a and 8b. Two side sections of the support 81 are rotable about an axis relative to one another so that the angle of penetration of the applicators 8a and 8b may be adjusted. In FIG. 4, there is shown a buccal applicator shaped to fit against the palate of a subject, which in this embodiment reaches rearwardly to the cartilaginous portion of the soft palate. The front portion of the applicator 138 comprises a clip 140 arranged so as to be able to be placed over the front teeth, so as to enable easy positioning of the applicator. The applicator may in addition be kept in position by pressure applied by the tongue. The electrical and electro-magnetic connection of the energy applicator 138 with the energy transmission line 14 (FIG. 1) is effected by way of a connector portion 141 playing the same role as the portion 19 of the energy applicator 8 shown in FIG. 1 or the portion 79 of the applicator 78 shown in FIG. 2, the surface of the applicator 138 being entirely or partially covered with an electrically conductive layer. The buccal energy applicator 138 may be equipped with one or more lines for transmission of luminous signals, consisting, for example, of one or more optical fibres or bundles of optical fibres incorporated into the body of the applicator and lying flush with the surface. FIG. 5 of the drawings shows an applicator for being held in the hand or between the teeth of a subject. The applicator comprises a clip or stop 140 as is also shown in FIG. 4 for abutting against the front teeth of a subject, thereby facilitating positioning of the applicator. The applicator shown in FIG. 5 comprises a body portion 142 which serves as a handle and also serves as a housing to house electric circuitry, one or more generators as in FIG. 1, and optionally batteries for supplying power to the one or more generators. A thumb switch 144 is provided for activating the one or more generators. Alternatively or additionally, the applicator may be provided with power lines 146 for connection to a power source, which may serve to activate generators or to charge rechargeable accumulators within the housing 142. Energy from the one or more generators and in particular electromagnetic energy of the nature discussed above is conveyed to electrode or emitter 148, which is shaped to fit against the palate of a subject, as shown in FIG. 4. The housing 142 and surround 150 of the electrode or emmitter 148 is of electrically non-conductive plastics material. Where desired, an optical fibre bundle may also be arranged to terminate at the surface of the transmitter 148.

Where the electrically induced energy to be applied to the brain of the subject is to include an electric current, electrodes 152 as shown in FIGS. 7a, 7b, or 7c are contacted with the head of the patient and current returned to the power source by electrically conductive line 154. The electrode shown in FIG. 7a is shaped for placing behind an ear of the subject, the electrode of FIG. 7b for placing on the temple of the subject, and the series of electrodes 152 for placing about the head of the subject with the aid of a head band 156 about the inside of which the electrodes are mounted.

Studies made with the aid of an encephologram of patients treated by the method of the invention with apparatus of the invention, have reflected that the method has a favourable normalising effect on the encephologram similar to the effect of a tranquilizer such as a benzodiazepine derivative. The general conclusion of the encephologram studies is that the electrotherapy procedure of the invention is effective in the treatment of a variety of different clinical states of disorders of the vegetative nervous system. The specific case reports above all refer to endonasal application. However, more recent studies, carried out with available endonasal probes inserted into the mouth of the subject rather than into the endonasal cavity, have reflected that entirely satisfactory results are achieved when the applicator is placed in the mouth of the subject. On the other hand, tests carried out with placement of the applicator outside of the head show little to no effect.

What we claim is:

1. A method of treating a subject suffering from anxiety neurosis and any accompanying neurovegetative disturbance, which comprises the step of applying to the brain of said subject a therapeutically effective amount of an electrically induced energy capable of influencing the vegetative nervous system of the brain, said electrically induced energy comprising rectangular d.c. pulses having a pulse duration of from 0.5 to 5 milliseconds at a voltage of from 10 to 100 millivolts with a repetition frequency of from 10 to 100 hertz, or a.c. pulses having a frequency of from 20 to 100 megahertz modulated with a frequency of modulation of from 2.5 to 6000 hertz, the application of said energy being performed by placing a suitably adapted energy applicator in the form of an emitter in the mouth or endonasal cavity of the subject and energizing the emitter so that the limbic system of the brain receives said electrically induced energy from the emitter.

2. A method according to claim 1, wherein said electrically induced energy comprises rectangular d.c. pulses having a pulse duration of from 0.5 to 5 milliseconds at a voltage of from 10 to 100 millivolts with a repetition frequency of from 10 to 100 hertz.

3. A method according to claim 1, in which the frequency of said pulses is adjusted dependent upon the response by the subject to the treatment.

4. A method in accordance with claim 1, wherein the application of said energy is performed by placing said emitter in the mouth of the subject and energizing the emitter.

5. A method in accordance with claim 1, wherein the application of said energy is performed by placing said emitter in the endonasal cavity of the subject and energizing the emitter.

6. Apparatus for treating a subject suffering from anxiety neurosis and any accompanying neurovegetative disturbance, comprising generator means for generating rectangular d.c. pulses having a pulse duration of from 0.5 to 5 milliseconds at a voltage of from 10 to 100 millivolts with a repetition frequency of from 10 to 100 hertz, or a.c. pulses having a frequency of from 20 to 100 megahertz modulated with a frequency of modulation of from 2.5 to 6000 hertz, and an energy applicator connected to said generator means, said energy applictor being shaped and sized to permit placement in the mouth or endonasal cavity of the subject and including emitter means for directing said electrically induced energy to the limbic system of the brain of the subject when said energy applicator is placed in the mouth or endonasal cavity of the subject and the generator means is activated.

7. Apparatus according to claim 6, in which said generator means is for generating rectangular d.c. pulses having a pulse duration of from 0.5 to 5 milliseconds at a voltage of from 10 to 100 millivolts with a repetition frequency of from 10 to 100 hertz.

8. Apparatus according to claim 6, in which the apparatus is of portable pocket size including a housing for housing said generator means and in which said energy applicator extends from said housing.

9. Apparatus according to claim 8, in which said energy applicator is shaped and sized to permit placement in the mouth and to fit against the palate of the subject.

10. Apparatus in accordance with claim 6, wherein said energy applicator is shaped and sized to permit placement in the mouth of the subject.

11. Apparatus in accordance with claim 6, wherein said energy applicator is shaped and sized to permit placement in the endonasal cavity of the subject.

* * * * *